(12) United States Patent
Fabry et al.

(10) Patent No.: US 8,767,986 B1
(45) Date of Patent: Jul. 1, 2014

(54) METHOD AND APPARATUS FOR HEARING AID SUBSCRIPTION SUPPORT

(75) Inventors: David Alan Fabry, Miami Beach, FL (US); Mark Mercury, Minneapolis, MN (US); Christopher Larry Howes, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 140 days.

(21) Appl. No.: 12/980,998

(22) Filed: Dec. 29, 2010

Related U.S. Application Data

(60) Provisional application No. 61/323,162, filed on Apr. 12, 2010.

(51) Int. Cl.
*H04R 25/00* (2006.01)
*H04R 29/00* (2006.01)

(52) U.S. Cl.
USPC ............................................ 381/314; 381/60

(58) Field of Classification Search
USPC .............................. 381/312–315, 60; 600/559
See application file for complete search history.

(56) References Cited

U.S. PATENT DOCUMENTS

| | | | |
|---|---|---|---|
| 6,556,686 B1 * | 4/2003 | Weidner | 381/312 |
| 6,785,394 B1 * | 8/2004 | Olsen et al. | 381/312 |
| 8,166,312 B2 | 4/2012 | Waldmann | |
| 2001/0055404 A1 * | 12/2001 | Bisgaard | 381/314 |
| 2004/0071304 A1 * | 4/2004 | Yanz et al. | 381/312 |
| 2007/0052548 A1 | 3/2007 | Hankin et al. | |
| 2008/0240453 A1 * | 10/2008 | Westergaard | 381/60 |
| 2011/0051967 A1 | 3/2011 | Lim et al. | |

* cited by examiner

*Primary Examiner* — Curtis Kuntz
*Assistant Examiner* — Sunita Joshi
(74) *Attorney, Agent, or Firm* — Schwegman, Lundberg & Woessner, P.A.

(57) ABSTRACT

A hearing aid distribution and service plan based on periodic subscription serves a wide range of hearing aid users with various needs for functionality and considerations for financial or value. One or more codes are provided for each hearing aid to allow for fitting by an authorized professional and enablement of one or more specified functions for a specified period. In various examples, the present hearing aid includes hearing assistance circuitry with a programming lock configured to receive an unlocking signal and a locking signal. In various examples, a hearing aid fitting device for communicating with a hearing aid includes a user interface configured to receive a lock code enabling a lock functionality that allows the hearing aid to be unlocked for fitting and locked for preventing from the fitting. The present application includes variations of a method for subscription-based hearing aid distribution.

22 Claims, 7 Drawing Sheets

Fig. 1

USER PREFERENCES

GENERAL

TARGET AUDIENCE
STARKEY USA ▼

LOCALE
ENGLISH- NEUTRAL ▼

DEFAULT GRAPHICAL VIEW
REAL EAR RESPONSE (dB SPL) ▼

DEFAULT FITTING VIEW
QUICKFIT ▼

HEARING AID LOCK CODE
xxxxxxxxxxxxxxxxxxxxxxxxxxxxxxxxxxxxxxxx
xxxxxxxxxxxxxxxxxxxxxxxxxxxxxxxxxx
xxxxxxxxxxxxxxxxxxxxxxxxxxxxxxxxxx

☐ – ☐ – ☐ – ☐ – ☐

( CANCEL )

☒ DISPLAY TOOL TIPS
☐ DISPLAY TRESHOLDS AND UCLS
☒ DISPLAY SHADING ON SPL GRAPH
☒ DISPLAY MAX OUTPUT LINE ON ALL SPL GRAPHS
☐ SHOW SWEEP TECHNOLOGY SLEEP MODE OPTION
☐ DEFAULT EXPERT ASSISTANT TO ADVANCED VIEW
☒ PROMPT FOR SESSION DESCRIPTION
☐ SHOW MATRICES IN SELECT PRODUCTS
☒ LAUNCH AUTO PATH ON INITIAL READ
☐ DEFAULT PERFORMANCE VALUES REGION OPEN
☐ AUTOMATICALLY MUTE DEVICES WHEN DETECTED ( RESTORE TO INSPIRE DEFAULTS )

( OK )  ( CANCEL )  ( APPLY )

HEARING AID MANAGEMENT

HEARING AID SUBSCRIPTION

① ENTER SUBSCRIPTION CODE: LEFT [**********************] (ACTIVATE)  ACTIVATED: MM/DD/YY
VALID UNTIL: MM/DD/YY

① ENTER SUBSCRIPTION CODE: RIGHT [**********************] (ACTIVATE)  ACTIVATED: MM/DD/YY
VALID UNTIL: MM/DD/YY

PERFORMANCE UPDATE

IMPORTANT INFORMATION FOR PERFORMANCE UPDATE:
* THE UPDATE WILL TAKE 1-2 MINUTES USING THIS PROGRAMMER
* HEARING AIDS SHOULD BE REMOVED FROM THE EAR AS THERE MAY BE AUDIBLE ARTIFACTS DURING THE UPDATE
* DATA LOGGING WILL AUTOMATICALLY BE RESET
* AFTER THE UPDATE, PREVIOUSLY SAVED SESSIONS MAY NOT BE ABLE TO BE RETRIEVED AND USED WITH THE HEARING AID

CALL YOUR CUSTOMER SERVICE REPRESENTATIVE TO OBTAIN AN UPGRADED CODE AND THEN ENTER IT INTO THE FIELDS BELOW.
ONCE YOU HAVE ENTERED THE CODE CLICK UPDATE TO BEGIN UPDATING YOUR DEVICES.

② UPGRADE TO S-SERIES9NX                    ② UPGRADE TO S-SERIES9NX
ENTER CODE [          ]                      ENTER CODE [          ]

(UPDATE)

*Fig. 7*

SEND SUBSCRIPTION CODE

[CLEAR]

BILLING ACCOUNT NUMBER:

SERIAL NUMBER:  LEFT                    [GENERATE]         CODE: EG3EJBNBC

RIGHT                   [GENERATE]         CODE: EG3EJBNBC

EXPIRATION DATE: 11/6/2009  (MM/DD/YY)

SEND EMAIL TO:   MARK.MERCURY@STARKEY.COM   [SEND]        [ALL HISTORY]

CUSTOMER SERVICE REP: MS/MERCURYM

| ACCOUNT NUMBER | SUBSCRIPTION CODE | ISSUER | DATE ISSUED | EXPIRATION DATE |
|---|---|---|---|---|
| 20908 | EG3EJBNBC | MS/MERCURYM | 11/6/2009 | 11/6/2009 |

METHOD AND APPARATUS FOR HEARING AID SUBSCRIPTION SUPPORT

CLAIM OF PRIORITY

The present application claims the benefit under 35 U.S.C. §119(e) of U.S. Provisional Patent Application Ser. No. 61/323,162, filed on Apr. 12, 2010, which is incorporated herein by reference in its entirety.

TECHNICAL FIELD

This document relates generally to hearing aids and more particularly to a system that supports subscription-based hearing aid distribution.

BACKGROUND

A significant population of candidates for using hearing aids reportedly decided not to obtain hearing aids due to financial or value considerations. Some of them indicated that they could not afford hearing aids. On the other hand, "luxury" buyers want the latest technology and are willing to pay premium price for state-of-the-art devices that offer ease of service and provide good user outcomes. Some candidates are not willing to commit to the replacement cycle of a typical hearing aid that is about four to six years. Therefore, there is a need for distributing hearing aids that satisfy the needs of a wide range of candidates.

SUMMARY

A hearing aid distribution and service plan based on periodic subscription serves a wide range of hearing aid users with various needs for functionality and considerations for financial or value. One or more codes are provided for each hearing aid to allow for fitting by an authorized professional and enablement of one or more specified functions for a specified period.

In various examples, the present subject matter includes a hearing aid, including hearing assistance circuitry programmable for performing one or more hearing assistance functions; and a programming lock configured to receive an unlocking signal and a locking signal, allow reprogramming of the hearing assistance circuitry in response to the unlocking signal, and disallow the reprogramming in response to the locking signal. In certain variations, the hearing aid further includes a subscription timer configured to receive a subscription signal and enable one or more functions of the hearing assistance circuitry for a subscription period specified in the subscription signal. In certain cases, the subscription timer is configured to reset the hearing assistance circuitry to a default setting upon expiration of the subscription period. In certain approaches, the programming lock is configured to store a lock code allowing the hearing aid to be unlocked for fitting and locked after the fitting.

In various examples, the present subject matter includes a hearing aid fitting device for communicating with a hearing aid, including a user interface configured to receive a lock code enabling a lock functionality that allows the hearing aid to be unlocked for fitting and locked for preventing from the fitting, and a fitting module configured to decode the received lock code and check for match between the received lock code and a stored lock code in the hearing aid. In certain variations of the hearing aid fitting device, the user interface is further configured to receive a subscription code enabling functionality of the hearing aid for a subscription period, and the fitting module is further configured to decode the subscription code. In some variations of the hearing aid fitting device, the user interface is configured to allow entry of a first subscription code for a left hearing aid device of the hearing aid and a second subscription code for a right hearing aid device of the hearing aid.

The present application includes variations of a method for subscription-based hearing aid distribution, including providing a hearing aid programmable for one or more specified functions and locked to prevent reprogramming of the one or more specified functions, and providing a lock code allowing for unlocking of the hearing aid to enable reprogramming of the one or more specified functions. In certain variations, the method includes storing the lock code in the hearing aid, and enabling the reprogramming in response to receiving a matching lock code by a user interface of a hearing aid fitting device. Variations of the approach provide a subscription code allowing for enabling of the one or more specified functions for a subscription period. In some cases the approach provides a first subscription code for a left hearing aid device of the hearing aid and a second subscription code for a right hearing aid device of the hearing aid. Variations also allow for resetting the hearing aid to a default setting upon expiration of the subscription period. An option includes setting the hearing aid to a flat gain setting upon expiration of the subscription period. Other variations include restarting or extending the subscription period in response to a renewal of subscription, providing an automatic reminder for the renewal of subscription, and extending the subscription for each remake or repair of the hearing aid.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

This document discusses a hearing aid system that allows for a subscription-based distribution of hearing aids. A hearing aid is adjusted in a process referred to as "fitting" to be tuned to its wearer's particular conditions and needs. After an initial fitting, the wearer may desire additional fitting processes such that the hearing aid remains tuned for changing conditions and needs. The present hearing aid system allows only authorized professionals to perform fitting for hearing aid wearers who are current subscribers. In this document, an "authorized professional" includes an audiologist or other trained caregiver who is provided with one or more codes by a manufacturer or an authorized distributor of hearing aids. The one or more codes allow for fitting of a hearing aid of a current subscription and/or prescribed use of the hearing aid by the authorized professional according to terms and conditions of the subscription. In one embodiment, a lock code is provided to unlock the hearing aid for its fitting and lock the hearing aid after the fitting. In a further embodiment, a subscription code is provided to enable one or more specified functions of the hearing aid for an amount of time specified by the terms and conditions of the subscription.

Figure 1:
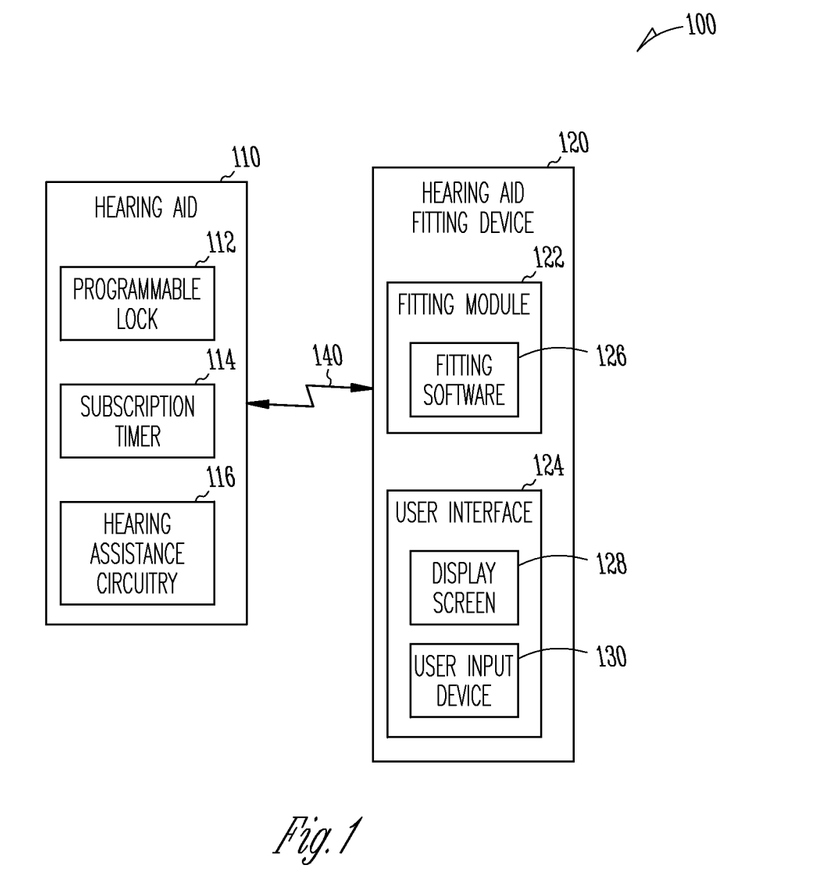
FIG. 1 is a block diagram illustrating an embodiment of a hearing aid system including a hearing aid and a hearing aid fitting device including a display screen.

FIG. 1 is a block diagram illustrating an embodiment of a hearing aid system 100 including a hearing aid 110 and a hearing aid fitting device. Hearing aid 110 represents one or more hearing aids undergoing a live fitting, while being discussed below as one hearing aid. For example, hearing aid 110 may represent a hearing aid device for use in the right ear and another hearing aid device for use in the left ear in a live binaural fitting. Thus, hearing aid 110 as discussed below represents each of the one or more hearing aids undergoing a live fitting.

In the illustrated embodiment, hearing aid 110 includes a programming lock 112, a subscription timer 114, and hearing assistance circuitry 116. Programming lock 112 prevents unauthorized reprogramming of hearing aid 110, such that fitting must be initiated by an authorized professional. Subscription timer 114 limits the time of usage of hearing aid 110 according to a subscription period. In various embodiments, hearing aid 110 includes either or both of programming lock 112 and subscription timer 114, depending on the hearing aid distribution plans of the manufacturer and/or the authorized distributors. Hearing assistance circuitry 116 is programmable to perform one or more specified hearing assistance functions;

Programming lock 112 receives locking and unlocking signals. In response to each locking signal, programming lock 112 disallows reprogramming of hearing assistance circuitry 116. In response to each unlocking signal, programming lock 112 allows reprogramming of hearing assistance circuitry 116. Such reprogramming is performed during fitting of hearing aid 110 to adjust the performance of hearing assistance circuitry 116. Subscription timer 114 receives a subscription signal and enables one or more specified functions of hearing assistance circuitry 116 for a subscription period specified in the subscription signal. Upon expiration of the subscription period, subscription timer 114 disables the one or more specified functions. In one embodiment, subscription timer 114 resets hearing assistance circuitry 116 to specified default settings upon the expiration of the subscription period.

In various embodiments, programming lock 112, subscription timer 114, and hearing assistance circuitry 116 are each implemented in one or more of hardware, software, and firmware of hearing aid 110. Prior to fitting, hearing aid fitting device 120 receives and decodes a lock code that enables transmission of the locking and unlocking signals to hearing aid 110. The locking and unlocking signals are unique to each specific hearing aid 110. In an embodiment in which the fitting is provided based on periodic subscription, hearing aid fitting device 120 receives and decodes a subscription code and transmits the subscription signal to hearing aid 100 to enable the one or more specified functions for the subscription period specified by the subscription code.

Hearing aid fitting device 120 is a computer or computer-based device that includes a fitting module 122 and a user interface 124. During a fitting session, hearing aid fitting device 120 communicates with hearing aid 110 via a wired or wireless communication link 140. In various embodiments, fitting module 122 includes portions of a processing circuit programmed with a fitting software 126, such as a microprocessor and a storage circuit storing fitting software 126. In various embodiments, fitting module 122 receives and decodes one or more of the lock code and the subscription code. In one embodiment, the one or more of the lock code and the subscription code are decoded by fitting software 126. Fitting module 122 is programmed to decode the lock code and allow unlocking of hearing aid 110 for a valid lock code. In various embodiments, fitting module 122 is also programmed to decode from the subscription code information including, but not limited to a serial number of hearing aid 110 associated with the subscription code, the end date of the current subscription, and/or the wearer's account number associated with the subscription code.

User interface 124 includes a display screen 128 and a user input device 130. In one embodiment, at least part of user input device 130 is integrated with display screen 128 as an interactive screen responsive to touch. In various embodiments, user input device 130 includes a keyboard, a mouse, a touch pad, a trackball, and/or display screen 128.

The reception and decoding of the lock code and the subscription code by user interface 124 and fitting module 122 are discussed below by way of example, and not by way of limitation, with reference to FIGS. 2-7. The design including various features and labels of the dialog windows illustrated in FIGS. 2-7 are examples and may be rearranged and renamed without departing from the present subject matter. In one embodiment, hearing aid system 100 is programmed to use the lock code to allow fitting of hearing aid 110. In another embodiment, hearing aid system 100 is programmed to use the lock code to allow fitting of hearing aid and the subscription code to enable the functionality of hearing aid 110 for the time period specified by the subscription. The dialog windows to be presented on display screen 128, as discussed below with reference to FIGS. 2-7, provide for interaction between the authorized professional and hearing aid system 100 related to the lock and subscription codes. Such dialog windows are part of the fitting interactions with the authorized professional provided by fitting software 126. In various embodiments, fitting module 122 is programmed to perform the fitting functions as discussed in this document, including the interaction with the authorized professional through user interface 124.

Figure 2:
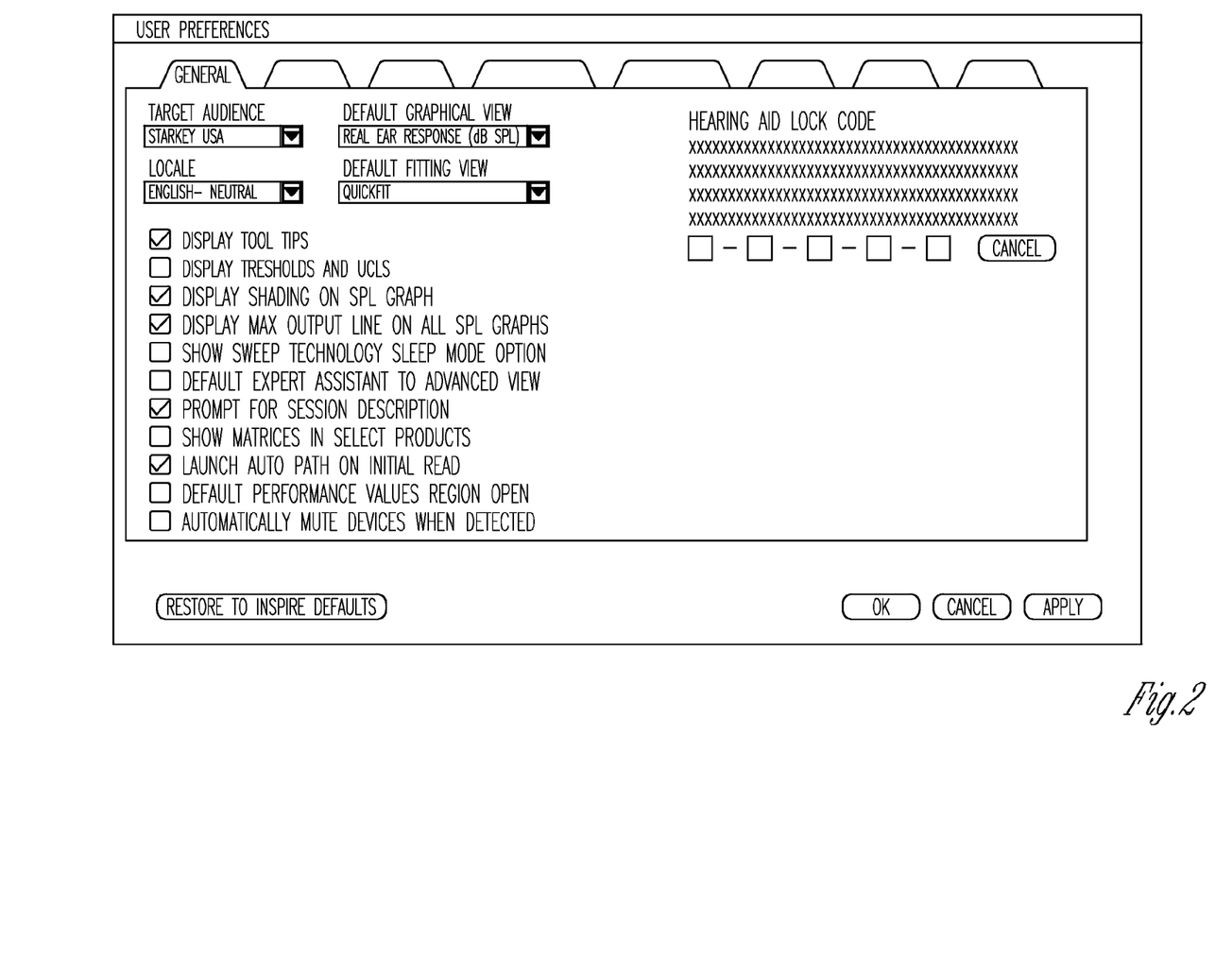
FIG. 2 is an illustration of an embodiment of a "User Preferences" dialog window to be presented on the display screen.

FIG. 2 is an illustration of an embodiment of a "User Preferences" dialog window to be presented on display screen 128. In the illustrated embodiment, a designated lock code field, labeled as "Hearing Aid Lock Code", in the User Preference dialog window allows for entry of a unique lock code for locking and unlocking hearing aid 100. In other embodiments, such a lock code field is designated in any window that is to be presented before the fitting starts. In one embodiment, each lock code consists of a 4-digit, non-case sensitive combination of alphabetic and numeric characters. The lock code field is displayed in the upper right corner of a General Preferences screen dialog within the User Preference dialog window with the following text appearing just below the "Hearing Aid Lock Code" field label: "Enter your 4-digit lock code in the fields below. The lock code must contain 4 characters (numbers or letters). If this field is left blank then the lock/un-lock functionality will be disabled." A "Clear" button is displayed next to the lock code field. When the Clear button is clicked, the entered lock code is erased from the lock code field. In other embodiments, each lock code consists of any combination of alphabetic, numeric, and other characters, subject to specified restraints. When the lock field is empty or when the authorized professional has deleted all the characters from the lock field, clicking the "OK" or "Apply" button displayed within the General Preferences dialog disables the lock functionality, thereby disallowing unlocking and locking of hearing aid 110. When the lock field contains any alphanumeric characters, clicking the 'OK' or "Apply" button displayed within the General Preferences dialog enables the lock functionality to allow the authorized professional to unlock and lock hearing aid 110 in response to each valid lock code, provided that the lock code is entered with the correct format.

Figure 3:
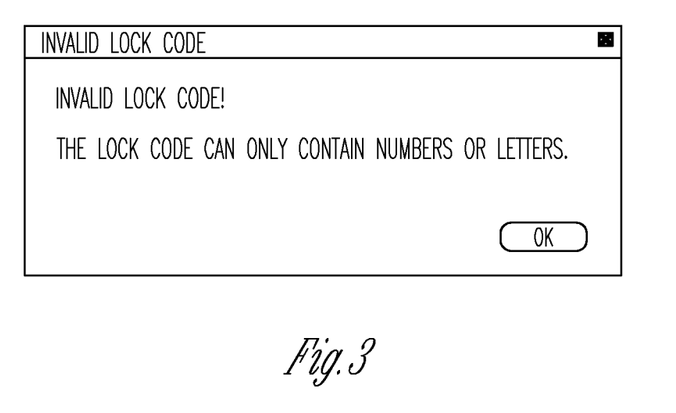
FIG. 3 is an illustration of an embodiment of an "Invalid Lock Code" dialog window to be presented on the display screen.

FIG. 3 is an illustration of an embodiment of an "Invalid Lock Code" dialog window to be presented on display screen 128. If the authorized professional enters a lock code in an invalid format and then clicks the "OK" or "Apply" button within the General Preferences dialog, the Invalid Lock Code dialog window appears with the following text: "Invalid Lock Code! The lock code can only contain numbers or letters." An "OK" button is presented within the Invalid Lock Code dialog window. Clicking this "OK" button immediately closes the Invalid Lock Code dialog window.

When the lock functionality has been enabled in response to a valid lock code, the authorized professional is provided with the option to lock or unlock hearing aid 110, or generally any hearing aid that is involved in a live fitting, by navigating to a Tools drop-down menu presented on display screen 128 and selecting the option "Lock Hearing Aid" or "Unlock Hearing Aid". If hearing aid 110 is not locked, the Tools drop-down menu displays the option "Lock Hearing Aid". If hearing aid 110 is locked, the Tools drop-down menu displays the option "Unlock Hearing Aid". If the lock functionality is not enabled, the lock/unlock option are displayed in within the Tools drop-down menu but disabled for selection, such as being grayed out (e.g., with the option "Lock Hearing Aid" appearing as grayed out).

When the authorized professional chooses the "Lock Hearing Aid" option from the Tools drop-down menu, the lock code (as entered in the User Preferences dialog window) is transmitted to hearing aid 110 to be stored in programming lock 112, such as by being burned into an erasable programmable read only memory (EPROM) in hearing aid 110. Once the lock code is stored in hearing aid 110, it is used by fitting module 122 during each follow-up visit to check for match between the lock code stored in hearing aid 110 and the lock code entered during that follow-up visit. If these lock codes do not match, or if no lock code has been entered during the follow-up visit, a dialog window appears to prompt the authorized professional to enter the correct lock code to continue with the fitting. A lock icon appears in the upper right corner of a fitting screen that corresponds to the locked hearing aid 110. A lock icon also appears next to a hearing aid status icons on the bottom right of the fitting screen. In a binaural fitting, selecting the "Lock Hearing Aid" option from the Tools drop-down menu locks only the hearing aid that corresponds to the state of binaural view control. For example, if the authorized professional is in a live binaural fitting and is in a left monaural view, then selecting the "Lock Hearing Aid" aid option from the Tools drop-down menu will only lock the left hearing aid.

When the authorized professional chooses the "Unlock Hearing Aid" option from the Tools drop-down menu, the lock code that is stored in hearing aid 110 is erased. The lock icon that appears in the upper right corner of the fitting graph of disappears. In a binaural fitting, selecting the "Un-lock Hearing Aid" option from the Tools drop-down menu unlocks only the hearing aid that corresponds to the state of binaural view control. For example, if the authorized professional is in a live binaural fitting and is in a left monaural view, then selecting the "Unlock Hearing Aid" aid option from the Tools drop-down menu will only un-lock the left hearing aid.

Once hearing aid 110 has been locked, no live fitting can be performed to hearing aid 110 unless hearing aid 110 is unlocked by entering a lock code that matches the lock code stored in the locked hearing aid 110. If communication has been established between the locked hearing aid 110 and hearing aid fitting device 120, but the lock code stored in hearing aid 110 is not matched by a lock code stored in fitting module 122, the authorized professional is allowed to select hearing aid 110 from a discovery toast dialog for a live fitting. The authorized professional selects "Quick Connect" to establish a live fitting session and receives a dialog prompt as illustrated in FIG. 4 before the live fitting session is established.

Figure 4:
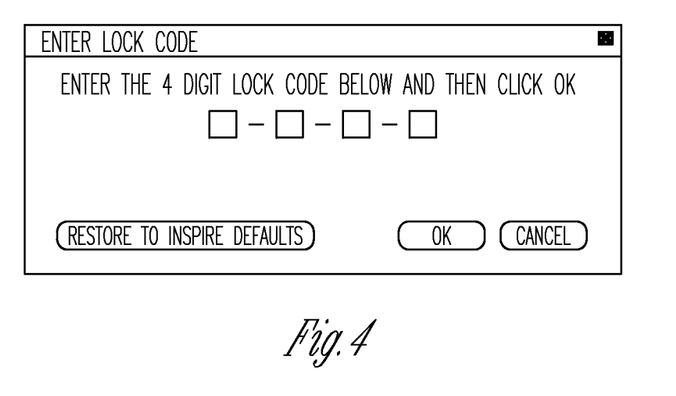
FIG. 4 is an illustration of an embodiment of an "Enter Lock Code" dialog window to be presented on the display screen.

FIG. 4 is an illustration of an embodiment of an "Enter Lock Code" dialog window to be presented on display screen 128. The Enter Lock Code dialog window contains a text filed, a lock code field, an "OK" button, a "Cancel" button, and a "Reset to Full-on Gain" button. The text field displays "Enter the 4-digit lock code below and then click 'OK'". The lock code field allows entry of the 4-digit lock code. Clicking of the OK button initiates a validation process in which fitting module 122 checks whether the lock code entered matches the lock code stored in hearing aid 110. Clicking the Cancel button closes the Enter Lock Code dialog window, thereby terminating the live fitting session. Clicking the Reset to Full-on Gain button launches a second dialog as illustrated in FIG. 5.

Figure 5:
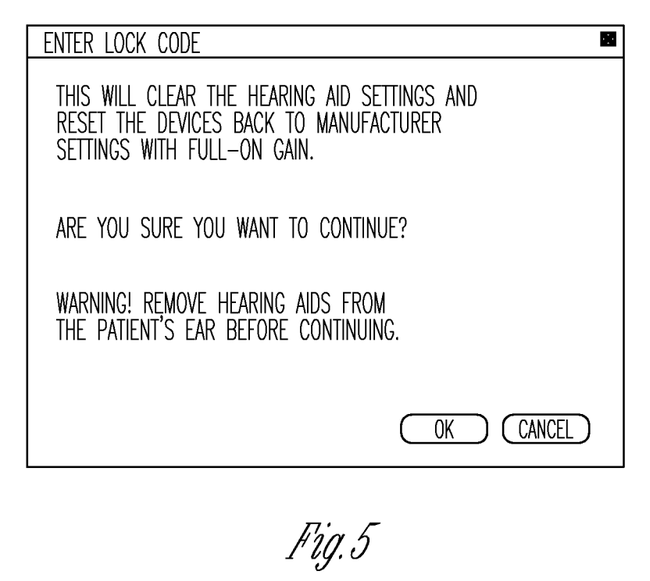
FIG. 5 is an illustration of an embodiment of the Enter Lock Code dialog window presenting a warning message.

FIG. 5 is an illustration of an embodiment of the Enter Lock Code dialog window presenting a warning message. In response to the clicking of the Reset to Full-on Gain button, the Enter Lock Code dialog window displays the text: "This will clear the hearing aid settings and set the devices back to manufacturer settings with full-on gain", a question "Are you sure you want to continue?" and a warning message "Warning! Remove hearing aids from the patient's ear before continuing." An "OK" button and a "Cancel" button are presented to allow the authorized professional to decide whether to proceed. In one embodiment, the warning message flashes in red bold text. A Close icon is located in the top left corner of the Enter Lock Code dialog window. Clicking the Close icon closes the Enter Lock Code dialog window and cancels the operation.

Figure 6:
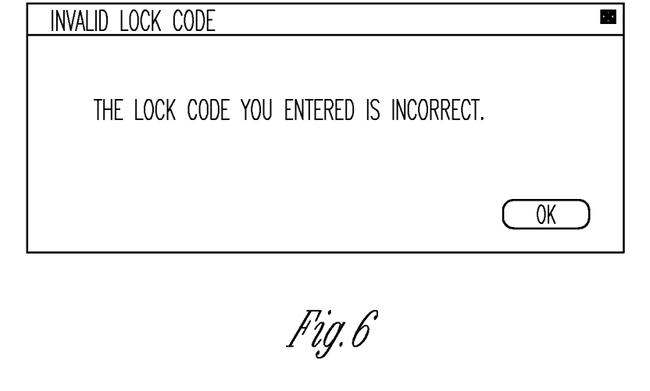
FIG. 6 is an illustration of an embodiment of another "Invalid Lock Code" dialog window to be presented on the display screen.

FIG. 6 is an illustration of an embodiment of another "Invalid Lock Code" dialog window to be presented on display screen 128. If the authorized professional enters the lock code that matches the lock code stored in hearing aid 100 and then clicks "OK" in the Enter Lock Code dialog window, this dialog window closes and the live fitting session is established. If the authorized professional enters a code that does not match the lock code stored in hearing aid 110 and then clicks OK, the Invalid Lock Code dialog window appears and displays the text "The lock code you entered is incorrect" and an "OK" button. In one embodiment, clicking this "OK" button allows the authorized profession to reenter the lock code in the Enter Lock Code dialog window.

Figure 7:
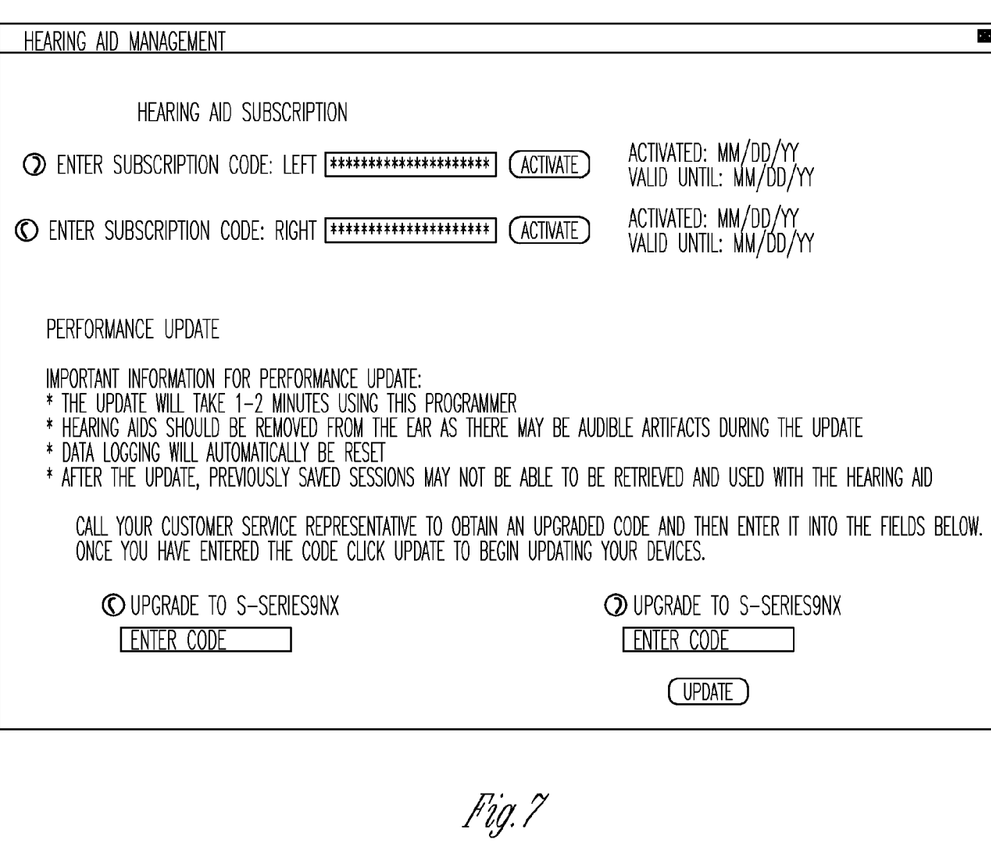
FIG. 7 is an illustration of an embodiment of a "Hearing Aid Management" dialog window to be presented on the display screen.

FIG. 7 is an illustration of an embodiment of a "Hearing Aid Management" dialog window to be presented on display screen 128. The Hearing Aid Management dialog window allows the authorized professional to enter one or more subscription codes that control the duration of programmed functionality of hearing aid 110. In one embodiment, hearing aid 110 receives the subscription signal including encrypted codes that represent a decoded subscription code and accordingly sets specified number of hours of usage. Once the specified number of hours expires, hearing aid 110 is reverted back to a default setting. In one embodiment, the firmware of hearing aid 110 assumes a 12-hour daily usage as soon as the subscription code becomes active. Thus, by default, hearing aid 110 is set for 4380 hours of usage once a subscription code associated with an annual (365-day) subscription has been activated. The total number of hours of usage is updated, for example when hearing aid 100 is being fitted, if the subscription is renewed or extended before its expiration. In one embodiment, the total number of hours of usage is recalculated based on an average daily use of hearing aid 110 that is stored in a data log in hearing aid 110. In one embodiment, if a subscription expires before being renewed, hearing aid 110 is automatically set to a flat 10 dB gain setting. In one embodiment, subscription activation dates are date stamped within hearing aid fitting device 120. If a subscription ends before one year, hearing aid 110 is automatically reactivated once it is connected to hearing aid fitting device 120. The firmware of hearing aid 110 recalculates the additional hours needed to re-enable hearing functionality to make it to the one year mark. This will involve a re-calculation based on the data log average daily usage counter. After healing aid 110 is set to default settings after expiration of the subscription, it may be reactivated to resume functionality at the programmed settings in response to renewal of the subscription.

In one embodiment, hearing aid 110 is programmed to trigger an automatic reminder for renewal of subscription. As soon as hearing aid 110 detects a specified number of remaining hours of usage, such as 200 hours, it produces a voice indicator, such as "Make Appointment". As soon as hearing aid 110 detects another specified number of remaining hours of usage, such as 50 hours, it produces the voice indicator again to remind the wearer to renew the subscription. In one embodiment, functions related to renewal of subscription are performed by the firmware of hearing aid 110.

In one embodiment, a subscription is extended for each remake or repair performed on hearing aid 100. For example, an annual subscription is to remain active for 365 days (specified in hours of usage). If there is a remake or a repair performed on hearing aid 110, the remake/repair facility adds an additional 30 days (specified in hours of usage) to the subscription.

In one embodiment, subscription for each hearing aid is repeated renewable for up to 4 years, after which the hearing aids becomes ineligible for renewal and continues to function at the prescribed settings. In one embodiment, the authorized professional is allowed to choose to extend the subscription by an additional year by requesting an additional subscription code prior to a warning period.

In various embodiments, the subscription code is unique for each hearing aid 110 and for each subscription period (such as one year). The functionality of hearing aid 110 in enabled in response to the subscription signal transmitted via wired or wireless link 140. The authorized professional activates a subscription by launching a dialog via the Tools menu and selecting the drop-down menu option "Hearing Aid Management". In response, the Hearing Aid Management dialog window as illustrated in FIG. 7 is displayed.

Various data entry fields and buttons are illustrated in FIG. 7 as features of the Hearing Aid Management dialog window. An "Enter Subscription Code: Left" field allows the authorized professional to enter in the unique subscription code for the left hearing aid device of hearing aid 110 that is connected to hearing aid fitting device 120 for its live fitting. An "Enter Subscription Code: Right" field allows the authorized professional to enter in the unique subscription code for the right hearing aid device of hearing aid 110 that is connected to hearing aid fitting device 120 for its live fitting. An "Activate" button is located next to each of the "Enter Subscription Code: Left" and "Enter Subscription Code: Right" fields. When the authorized professional clicks the Activate button, hearing aid 100 is instructed to terminate hearing aid functionality exactly one subscription period (such as one year) from the date this button is clicked. Once the Activate button is clicked, activation and expiration dates of the subscription are displayed, such as "Subscription Activated: MM/DD/YY; Subscription Valid until: MM/DD/YY". The "Valid Until MM/DD/YY" is expiration date of the subscription calculated based on the date and time kept in hearing aid fitting device 120. In one embodiment, the following message is displayed, such as above Enter Subscription Code fields: "Enter the subscription code that was provided to you by customer service into the field below and then click 'Activate Subscription'" and "If you do not have a subscription code, please call customer service and request one."

In one embodiment, hearing aid fitting device 120 asks each user for an account number to confirm the user's status as an authorized professional. When activation of a subscription is attempted, a dialog requesting the account number is presented in display screen 128. If the account number is not stored in hearing aid fitting device 120, the subscription code cannot be validated by hearing aid fitting device 120. Each subscription code that is distributed (e.g., by customer service department of the manufacturer) is encrypted to look for the account number that matches the subscription request. If the matching account is not found, the user is prompted to enter it into a dialog prompt.

In one embodiment, the authorized professional is required to obtain the subscription code, such as by contacting the manufacturer and its authorized representative. One or more subscription codes are tied to the name of the wearer requesting the subscription, as well as the hearing aid serial number. This allows for a manufacturer's data base to keep track of all of the unique subscription codes that have been sent out to various accounts.

Figure 8:
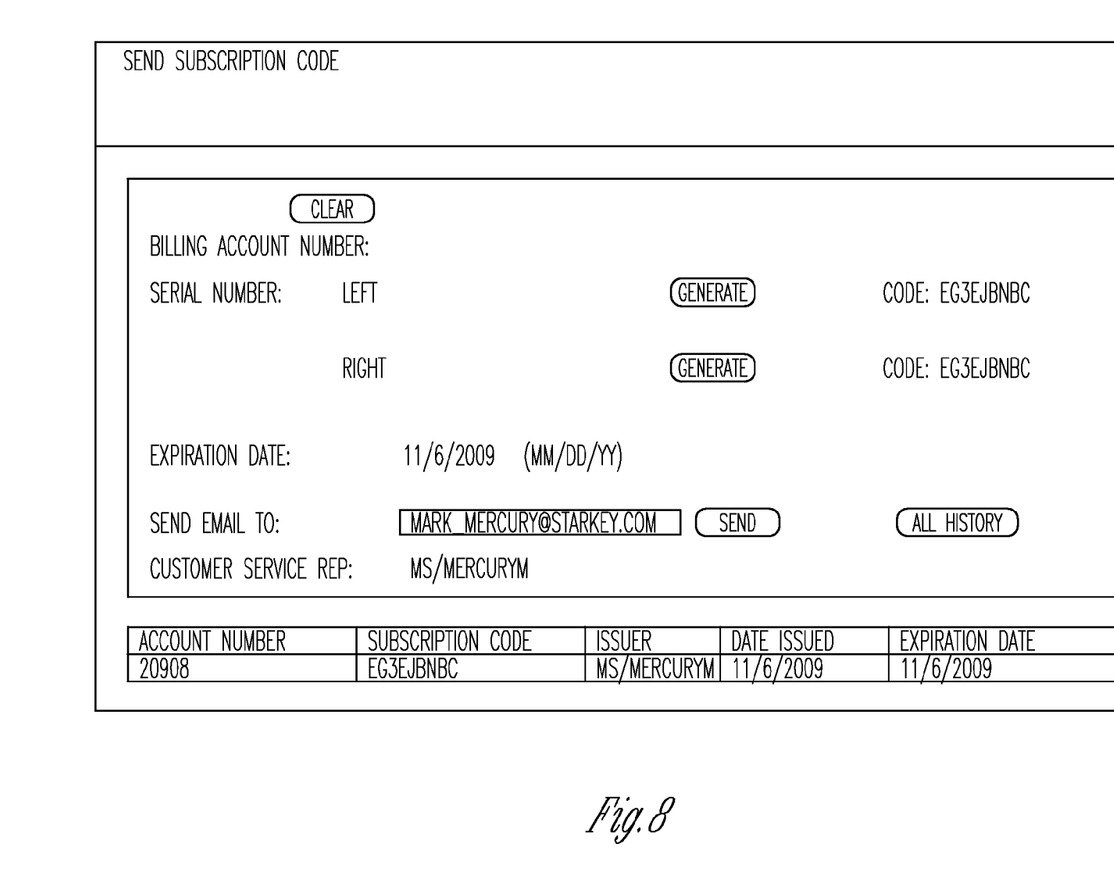
FIG. 8 is an illustration of an embodiment of a "Send Subscription Code" dialog window.

FIG. 8 is an illustration of an embodiment of a "Send Subscription Code" dialog window to be presented to a customer service representative of the hearing aid manufacturer or the authorized distributor. The customer service representative is required to enter information into the Send Subscription Code dialog window. A subscription code generator associated with the Send Subscription Code dialog window automatically generates a unique subscription code that can be e-mailed to the authorized professional.

Various features of the Send Subscription Code dialog window are illustrated in FIG. 8. A "Billing Account Number:" field allows for entry of the account number of the authorized professional wishing to retrieve a subscription code. "Serial Number" fields (for Left and Right) allow entry of the serial numbers for either the left and/or right hearing aids. "Generate" buttons located next to the Serial Number fields populate the "Code" fields each with a unique subscription code. The Code fields display the unique subscription codes. An "Expiration Date" field displays the expiration date of the subscription. A "Send E-mail To" field automatically populates with the e-mail address associated to the account number that has been entered. The Send E-mail To field can be overwritten with a different e-mail address. Clicking a "Send" button sends the unique subscription code to the e-mail address that is entered in the Send E-mail To field. The Send button is inactive until at least one serial number has been entered, a unique subscription code has been generated, and a valid e-mail address has been entered. A "Clear" button allows for clearance of all of the fields in the Send Subscription Code dialog window. A "Customer Service Rep" field automatically populates with the name of the customer service representative who is handling the request. Clicking an "All History" link results in display of all of the subscription code history for every account that has requested a subscription code in a "History" table. The History table is populated with all of the past subscription history information (e.g., account number, subscription codes, issuer, date issued, and expiration date) of the selected account number, unless the "All History" link is selected, in which case the subscription history of every account that has made a request shall be displayed.

When all of the customer information has been entered into the Send Subscription Code dialog window, the customer service representative must hit a "Send" button to send the subscription code to the authorized professional via email. Upon receiving the subscription code via e-mail, the authorized professional is able to enter the subscription code in the "Hearing Aid Management" dialog window. If the account number does not match the subscription code that has been entered, the authorized professional receives an error message dialog with the following text: "The subscription code you have entered does not match the account number <Account Number>. Try re-entering the subscription code again, or contact customer service if you keep getting this error." This text message is followed by an "OK" button allowing for closing of the dialog. If the serial number does not match the subscription code that has been entered, the authorized professional receives an error message dialog with the following text: "The subscription code you have entered does not match the serial number <display serial number>. Try re-entering the subscription code again, or contact customer service if you keep getting this error." This text message is followed by an "OK" button allowing for closing of the dialog. If neither the serial number nor the account number matches the subscription code that has been entered, the authorized professional receives an error dialog message with the following text: "The subscription code you have entered does not match the account number <Account Number> and does not match the serial number <serial number>. Try re-entering the subscription code again, or contact customer service if you keep getting this error." This text message is followed by an "OK" button allowing for closing of the dialog.

In one embodiment, the e-mail containing the subscription code contains the following information: subject Line: "Hearing Aid Subscription"; Sender: <email address of the customer service representative>; and body text: "Below are your subscription codes for the following devices: Left Hearing Aid (serial number): <subscription code>; Right Hearing Aid (serial number): <subscription code>; These subscription codes were requested on MM/DD/YY; This subscription is valid until: MM/DD/YY."

In various embodiments, the hearing aid manufacturer or authorized distributor is equipped with computers or computer-based systems programmed to allow hearing aid subscription codes to be sent out to customers. The subscription codes are managed by these computers or computer-based systems, which keep track of hearing aid subscription renewal-dates based on serial numbers of hearing aids. Remake and repair facilities of the hearing aid manufacturer or authorized distributor are equipped to bypass the locking of any hearing aid. The remake and repair facilities are also able to reset any remade or repaired hearing aid back to its correct time setting in order to keep the correct subscription date active.

Figure 9:
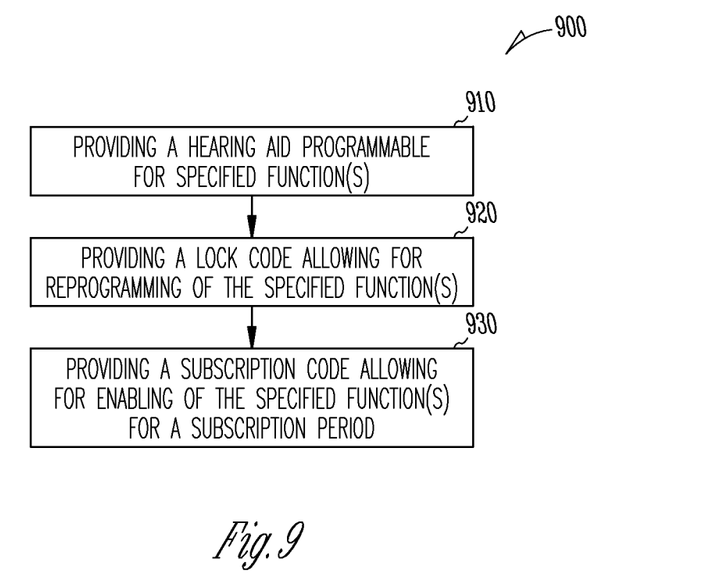
FIG. 9 is a flow chart illustrating a method for subscription-based hearing aid distribution.

FIG. 9 is a flow chart illustrating a method 900 for subscription-based hearing aid distribution. In one embodiment, performance of method is supported by hearing aid system 100 for distributing hearing aids such as hearing aid 110.

At 910, a hearing aid programmable for one or more specified functions is provided to a wearer. The hearing aid is programmed to a default setting and locked.

At 920, a lock code is provided to allow fitting of the hearing aid. The fitting includes reprogramming to adjust the one or more specified functions for the wearer. The lock code allows for unlocking of the locked hearing aid prior to the fitting and locking of the hearing aid upon completion of the fitting. In one embodiment, the lock code is provided to an authorized professional performing the fitting.

At 930, providing a subscription code enabling the one or more specified functions for a subscription period. The subscription period is restarted or extended in response to each renewal of the subscription. Upon expiration of the subscription period, the one or more specified functions are disabled, and the hearing aid is reset to its default setting.

The prevalent distribution model for hearing aids involves an average selling price (ASP) to the consumer that currently is about $2,000 per ear (for example, about $4,000 per pair) with approximately a 78% binaural fitting rate. The average replacement cycle for hardware is approximately 4 to 6 years. The average current annual cost is about $1,000 for two devices for the first two years, with average repair costs of about $200 per ear for years three and four when the initial warranty has expired (in a typical retail environment).

For many practitioners a "bundled" model of care is used to provide fitting and service for the life of the hearing aid in the initial cost of the device. The resulting "bundled" fee structure is approximately 2 to 3 times the device cost to the dispenser. Consequently, the cost of distribution is estimated to be about ⅔ of the final cost to the consumer. The cost of distribution is becoming more scrutinized over time.

The pricing discussed herein is subject to change over time, but the following description allows for an approach to subscription pricing that has not yet been accomplished in the hearing aid industry.

In one approach, the manufacturer uses a lock code, a subscription code, and a remote software support function as follows.

A professional who fits the device to the end-user wearer is the "Fitter." Using the following approach, the Fitter can selectively allow other professionals (also called "dispensers") to fit or adjust the hearing aids that the Fitter dispensed. This can also prevent other dispensers who are not authorized by the Fitter from fitting or adjusting the hearing aids that the Fitter dispensed. A lock code used by the Fitter provides the Fitter the option of allowing the wearer to have another profession fit or adjust his/her hearing aids provided by the Fitter. In various embodiments, the lock code is a six digit code. Other digits can be used without departing from the present subject matter.

A remote software tool allows the lock code and the subscription code to be used by the Fitter or the wearer. The Fitter or wearer can login using a user name and password to receive software or firmware updates or upgrades, perform diagnostic functions, participate in datalogging activities, and send or receive lock or subscription codes from the manufacturer. In one embodiment, this is done by logging into a website provided by the manufacturer. In one embodiment, this is done using a software module resident on the Fitter or wearer's computer to communicate with the manufacturer's server. In one embodiment, this communication is done via email. In some applications, a Hi-Pro, NOAH Link, or SpeedPro, or wireless programming interface is used to communicate the information. In various embodiments, the fitting software provided to the Fitter by the manufacturer contains the necessary communications support code. Other communication approaches may be used without departing from the scope of the present subject matter.

Depending on the interface, the software may allow the wearer or Fitter or authorized dispenser to optionally select upgrades to the functionality provided by the hearing aid. This allows the manufacturer the option of providing enhanced continuing support in the form of software and firmware upgrades that can be purchased or subscribed to by the wearer for increased listening benefits (and other potential uses).

In one embodiment, the wearer can purchase software or firmware upgrades that improve algorithm performance, provide additional features or enhancements, or services that can be used with the hearing aids that are additional offerings not related specifically to hearing aids themselves. For example, the service can provide a feature which provides programmable medication reminders to the wearer. The service can provide a reading service or a streaming audio service for listening to performances or creative works. Other services are possible and too numerous to mention herein. Some of the additional hearing related features include, but are not limited to enhanced directional microphone performance, acoustic scene analysis, improved feedback cancellation algorithms, improved noise reduction algorithms, improved volume control features, sweep enhancements, T2 performance, and combinations thereof. Although these enhancements reside on the hearing aid, they are facilitated through the software using synchronous or asynchronous programming using NOAH, NOAHLink, Speedport, or wireless programming interface and lock and/or subscription codes.

Results of MarkeTrak VII (Kochkin, 2007) reveal that nearly 3 in 10 respondents indicated that financial or value considerations impacted their decision not to obtain hearing aids. 22% indicated that they could not afford hearing aids. On the other end of the spectrum "luxury" buyers and early adopters want the latest technology and are willing to pay premium price for devices that are "state-of-the art, offer ease of service, and provide good user outcomes. The combination of "luxury" buyers and "skeptics" who are worried that they will outlive their conventional hearing aids (4-6 year replacement cycle) provides an opportunity for an altered business model concept with annual subscription service with lock and subscription codes that are enabled/disabled by either the Fitter or the manufacturer.

Thus, a "shared" benefit in partnership exists between the manufacturer and Fitter that uses a 3-4 year payment cycle. A four year subscription approach is proposed; however, it is understood that the number of years, payments, terms and conditions, and features may vary without departing from the scope of the present teaching.

In Year One of a proposed four year cycle, the wearer is fit with device(s) and pays the Fitter approximately $1,200 per ear for the hearing aids. (It is understood that the payment amounts may vary, but these are proposed based on current market rates and current purchase options). When the payment is received from the wearer, subscription codes are transmitted to the hearing aid(s) by the fitting software automatically (by the Fitter or by the manufacturer), or manually by the Fitter or by the manufacturer, or manual entry by the wearer. The Fitter may choose lock codes that allow the Fitter to authorize other dispensers/professionals to adjust or fit the devices. That way if the wearer moves or is on travel, the Fitter can control which professional will perform the necessary services and can work together to serve the customer. In various approaches, the lock codes may be disabled via the fitting software and when hearing aid is coupled to a programmer (including wireless communications). In this same Year One the fitter and manufacturer would receive $600 per ear. Devices would have protections, such as a three year loss and damage (single event) warranty and have fully upgradable firmware throughout a three year term to provide the best and latest functionality during that time.

In Year Two the wearer would hear an audible prompt, such as a voice or tone or other prompt, within weeks of the anniversary of the initial fitting indicating that the patient should contact the Fitter to enter new subscription codes for the next 12 months. The audible prompts may indicate that the device would be disabled if new subscription codes are not obtained within a particular timeframe. To prevent liability, devices may revert to simplified operation to provide "flat" 20-dB gain across all frequencies with peak-clipping limiter when operating in the unlicensed mode. When the wearer goes to obtain the new subscription codes a charge of $1,200 for the annual subscription fee is tendered and the codes are provided upon payment. According to one approach, in Year Two the Fitter would receive $800 and the balance of $400 would go to the manufacturer. The Repair and Loss/Damage Warranty (if not used) would remain in effect.

In Year Three, around the anniversary of the initial fitting the wearer would hear another set of audible prompts. The prompts may function like they did at Year Two or may differ, depending on the desired offering. When the wearer returns to the Fitter to receive the subscription codes, the wearer pays another $1,200. In Year Three the fitter receives about $900 and the remaining $300 is received by the manufacturer.

In Year Four (which is optional, and can be tailored as desired by the offering), around the anniversary of the initial fitting the wearer would hear another set of audible prompts. The prompts may function like they did at Year Two and/or Year Three, or may differ, depending on the desired offering. When the wearer returns to the Fitter to receive the subscription codes, the wearer pays another $1,200. In Year Four the fitter receives the entire payment of $1,200 and none of it goes to the manufacturer.

The foregoing number of years, costs, allocations, and handling of codes are adjustable and flexible and can be changed for different offerings. Therefore, these details are intended to demonstrate the present subject matter and not intended in an exhaustive, exclusive, or limiting sense.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A hearing aid, comprising:
hearing assistance circuitry programmable for performing one or more hearing assistance functions;
a programming lock configured to store a lock code and receive an unlocking signal and a locking signal, allow reprogramming of the hearing assistance circuitry to adjust the one or more hearing assistance functions and erase the stored lock code in response to the unlocking signal including a lock code matching the stored lock code, and disallow the reprogramming and store a received lock code in response to the locking signal with which the received lock code is transmitted to the hearing aid; and
a subscription timer configured to receive a subscription signal and enable the one or more hearing assistance functions of the hearing assistance circuitry and allow for the reprogramming for a subscription period.

2. The hearing aid of claim 1, wherein the subscription timer is configured to reset the hearing assistance circuitry to a default setting upon expiration of the subscription period.

3. The hearing aid of claim 2, wherein the default setting comprises a flat gain setting.

4. The hearing aid of claim 1, wherein the programming lock is configured to allow the hearing aid to be unlocked for fitting and locked after the fitting.

5. The hearing aid of claim 4, comprising an erasable programmable read only memory (EPROM), and wherein the lock code is stored in the EPROM.

6. A hearing aid fitting device for communicating with a hearing aid, comprising:
a user interface configured to receive a lock code and a subscription code, the lock code enabling a lock functionality that allows the hearing aid to be unlocked for fitting and locked for preventing from the fitting, being transmitted to and stored in the hearing aid in response to the hearing aid being locked, allowing the locked hearing aid to be unlocked in response to a match between the received lock code and the stored lock code, and being erased from the hearing aid in response to the hearing aid being unlocked, the subscription code enabling functionality of the hearing aid and allowing for the fitting for a subscription period; and
a fitting module configured to decode the received lock code, check for the match between the received lock code and the stored lock code in the hearing aid when the lock functionality is enabled, and decode the subscription code.

7. The hearing aid fitting device of claim 6, wherein the user interface comprises a display screen and a dialog window presented on the dialog screen to allow entry of the lock code.

8. The hearing aid fitting device of claim 7, wherein the dialog window is configured to allow for setting the hearing aid back to manufacturer settings.

9. The hearing aid fitting device of claim 7, wherein the user interface is configured to allow programming of the stored lock code.

10. The hearing aid fitting, device of claim 6, wherein the user interface is configured to allow entry of a first subscription code for a left hearing aid device of the hearing aid and a second subscription code for a right hearing aid device of the hearing aid.

11. A method for subscription-based hearing aid distribution, comprising:
providing a hearing aid programmable for one or more specified functions and locked to prevent reprogramming of the one or more specified functions;
providing a lock code allowing for unlocking of the hearing aid to enable reprogramming of the one or more specified functions, the lock code being transmitted to and stored in the hearing aid in response to the hearing aid being locked and erased from the hearing aid in response to the hearing aid being unlocked; and
providing a subscription code allowing for enabling of the one or more specified functions and reprogramming of the one or more specified functions for a subscription period.

12. The method of claim 11, comprising enabling the reprogramming in response to receiving a matching lock code by a user interface of a hearing aid fitting device.

13. The method of claim 12, comprising allowing for locking of the hearing aid upon completion of the reprogramming.

14. The method of claim 11, comprising providing a first subscription code for a left hearing aid device of the hearing aid and a second subscription code for a right hearing aid device of the hearing aid.

15. The method of claim 11, comprising resetting the hearing aid to a default setting upon expiration of the subscription period.

16. The method of claim 15, comprising setting the hearing aid to a flat gain setting upon expiration of the subscription period.

17. The method of claim 15, further comprising restarting or extending the subscription period in response to a renewal of subscription.

18. The method of claim 17, further comprising providing an automatic reminder for the renewal of subscription.

19. The method of claim 17, further comprising extending the subscription for each remake or repair of the hearing aid.

20. The hearing aid of claim 1, wherein the subscription timer is configured to enable the one or more hearing assistance functions of the hearing assistance circuitry for the subscription period specified in the subscription signal.

21. The hearing aid of claim 6, wherein the fitting module is configured to decode from the subscription code information including one or more of a serial number of the hearing aid associated with the subscription code, the subscription period, and a wearer's account number associated with the subscription code.

22. The method of claim 11, further comprising enabling the one or more specified functions for the subscription period specified by the subscription code.

* * * * *

UNITED STATES PATENT AND TRADEMARK OFFICE
CERTIFICATE OF CORRECTION

PATENT NO.       : 8,767,986 B1
APPLICATION NO.  : 12/980998
DATED            : July 1, 2014
INVENTOR(S)      : Fabry et al.

It is certified that error appears in the above-identified patent and that said Letters Patent is hereby corrected as shown below:

In the Claims

Column 13, line 14, Claim 1, delete "mare" and insert --more--, therefor

Column 14, line 7, Claim 10, delete "fitting," and insert --fitting--, therefor

Signed and Sealed this
Second Day of December, 2014

Michelle K. Lee
*Deputy Director of the United States Patent and Trademark Office*